United States Patent
Yamaguchi et al.

(10) Patent No.: US 9,869,626 B2
(45) Date of Patent: Jan. 16, 2018

(54) PARTICLE SIZE DISTRIBUTION MEASURING APPARATUS AND PARTICLE SIZE DISTRIBUTION MEASURING METHOD

(71) Applicant: HORIBA, Ltd., Kyoto-shi, Kyoto (JP)

(72) Inventors: Tetsuji Yamaguchi, Kyoto (JP); Tetsuya Mori, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 15/423,059

(22) Filed: Feb. 2, 2017

(65) Prior Publication Data

US 2017/0227437 A1    Aug. 10, 2017

(30) Foreign Application Priority Data

Feb. 5, 2016 (JP) .................. 2016-021302

(51) Int. Cl.
*G01N 15/02* (2006.01)

(52) U.S. Cl.
CPC ... *G01N 15/0211* (2013.01); *G01N 2015/025* (2013.01)

(58) Field of Classification Search
CPC .............. G01N 15/0211; G01N 2015/025
USPC ................................. 356/335–343
See application file for complete search history.

(56) References Cited

U.S. PATENT DOCUMENTS

2015/0056710 A1    2/2015  Reed et al.

FOREIGN PATENT DOCUMENTS

| JP | 08-136439 A | 5/1996 |
| JP | 2002022644 A | 1/2002 |
| JP | 2005249759 A | 9/2005 |
| WO | 0022407 A2 | 4/2000 |

OTHER PUBLICATIONS

Extended European Search Report dated Jun. 26, 2017 from corresponding European Application No./Patent No. 17154686.4-1553.

*Primary Examiner* — Tri T Ton
(74) *Attorney, Agent, or Firm* — Lucas & Mercanti, LLP

(57) ABSTRACT

Provided is a dynamic light scattering type particle size distribution measuring apparatus 100 capable of accurately measure the particle sizes of a sample obtained from slurry or the like. The dynamic light scattering type particle size distribution measuring apparatus 100 is configured to include: a filter member 6 that is interposed between any adjacent two of a light source 4, a cell 2, and a photodetector 5 and attenuates light passing therethrough; and an information processing device 8 that measures a particle size distribution multiple times with time and combines particle size distributions obtained at respective times of measurement to thereby calculate the particle size distribution of the whole of portions of the sample introduced at the respective times of measurement. In addition, the filter member 6 is also configured to be changeable to one having a different attenuation level at every time of measurement.

5 Claims, 4 Drawing Sheets

100: PARTICLE SIZE DISTRIBUTION MEASURING APPARATUS
2: CELL
4: LIGHT SOURCE
5: PHOTODETECTOR
6: FILTER MEMBER
8: INFORMATION PROCESSING DEVICE

PARTICLE SIZE DISTRIBUTION MEASURING APPARATUS AND PARTICLE SIZE DISTRIBUTION MEASURING METHOD

CROSS REFERENCE TO RELATED APPLICATION

This Application claims the priority of Japanese Patent Application No. JP 2016-021302 filed on Feb. 5, 2016, application which is incorporated herein by reference.

TECHNICAL FIELD

The present invention relates to a so-called dynamic light scattering type particle size distribution measuring apparatus and dynamic light scattering type particle size distribution measuring method adapted to measure a particle size distribution on the basis of a fluctuation in the intensity of scattered light obtained when radiating measurement light to a particle group dispersed in a medium.

BACKGROUND ART

Particle size distribution measuring apparatuses adapted to measure the particle size distribution of particles contained in a sample include ones of various types as disclosed in, for example, Patent Literatures 1 and 2.

Among such particle size distribution measuring apparatuses, there are ones of a so-called dynamic light scattering type. Further, among the dynamic light scattering type particle size distribution measuring apparatuses, there has been known a continuous measurement type particle size distribution measuring apparatus adapted to successively sample a portion of a sample to introduce the sampled portion into a cell, and measure particle sizes at every time of sampling (although since a certain measurement time is required for one time of particle size distribution measurement, it is strictly not the continuous measurement, but successive measurement).

When performing the measurement, particle sizes in a portion of the sample to be sampled and the concentration of the portion of sample to be sampled gradually change at every time of sampling, and the particle size distribution of the sample may not be identified.

For example, as disclosed in Patent Literature 3, in the case of a slurry type sample containing polish for polishing semiconductor wafers, such a phenomenon may occur. That is, unless sufficiently stirred, slurry causes a phenomenon where a particle size distribution differs locally. As a result, for example, depending on a sampling point in a storage tank of the slurry, the particle size distribution gradually changes with time.

For example, when sampling a portion of the slurry from the upper part of the storage tank in a state where in the slurry stored in the storage tank, a particle group having smaller particle sizes is unevenly distributed in the upper part, and in the bottom part, a particle group having larger particle sizes is unevenly distributed, inevitably, the particle size having smaller particle sizes is first introduced, and then with time, the group having larger particle sizes is gradually introduced. Accordingly, as described above, at every time of sampling, the particle size distribution gradually changes.

In such a case, as described in claim 3 of Patent Literature 1, usually, a particle size distribution is intermittently measured multiple times while continuously introducing a portion of a sample, and by combining particle size distributions obtained at the respective times of measurement, the particle size distribution of the whole of introduced portions of the sample is calculated.

Meanwhile, such a combination-based method for obtaining a particle size distribution has the advantage of being able to more accurately measure the particle size distribution. The reason for this is as follows.

That is, the spectrum of a particle size distribution is eventually obtained by software-based fitting. However, when there are multiple particle size peaks, the fitting is more difficult to perform, and for example, a smaller peak is hidden in an adjacent larger peak, thus causing a limit on the measurement accuracy of the smaller peak. On the other hand, the combined particle size distribution measurement makes it possible to perform easy fitting with high accuracy because the number of particle size peaks is small at every time of measurement.

CITATION LIST

Patent Literature

Patent Literature 1: Japanese Unexamined Patent Publication JP-A 8-136439
Patent Literature 2: Japanese Unexamined Patent Publication JP-A 2005-249759
Patent Literature 3: Japanese Unexamined Patent Publication JP-A 2002-22644

SUMMARY OF INVENTION

Technical Problem

However, depending on a sample to be measured, a particle size distribution and concentration are significantly different among a series of times of measurement for obtaining a combined particle size distribution, and therefore the intensities of scattered lights generated at the respective times of measurement may be significantly different from one another.

As a result, for example, when making the bandwidth of a photodetector adapted to detect a scattered light intensity appropriate for one time of measurement when the scattered light intensity is largest among the respective times of measurement, SN ratios at times of measurement when scattered light intensities are small are deteriorated, and as a result, desired measurement accuracy cannot be obtained, whereas when making the bandwidth of the photodetector appropriate for one time of measurement when the scattered light intensity is smallest, outputs of the photodetector at times of measurement when scattered light intensities are large are saturated, and as a result, the problem of being unable to perform measurement may occur.

The present invention is made in consideration of such problems, and a main intended object thereof is to make it possible for a continuously measurable dynamic light scattering type particle size distribution measuring apparatus to more accurately measure the particle size distribution of a sample, which changes at every time of measurement, such as slurry.

Solution to Problem

That is, the particle size distribution measuring apparatus according to the present invention is one including: a cell into which a portion of a sample that includes a medium and particles dispersed in the medium and arrives having a time distribution depending on a particle size or concentration is successively introduced; a light source that emits measurement light; a photodetector that receives scattered light from particles irradiated with the measurement light and detects the intensity of the scattered light; a filter member that is arranged in a predetermined position in a light path of the measurement light from the light source to the cell or a light path of the scattered light from the cell to the photodetector and attenuates the measurement light or the scattered light; and a measurement part that on the basis of a fluctuation in the scattered light intensity detected by the photodetector and the attenuation level of the filter member, measures the particle size distribution of a portion of the sample in the cell.

In addition, the measurement part is one that by measuring a particle size distribution every time a portion of the sample is introduced into the cell as well as combining particle size distributions obtained at respective times of measurement, calculates a particle size distribution of measured portions, the portions being introduced at the multiple times of measurement, respectively; and the filter member is configured to be changeable to one having a different attenuation level at every time of measurement.

Note that the change herein includes, in addition to replacing the filter member with one having a different attenuation level, increasing/decreasing the number of stacked filter members to make the attenuation level different, and the like.

Advantageous Effects of Invention

According to the present invention configured as described above, since in addition to the above-described basic effect due to combining the series of multiple particle size distribution measurements, by using a filter member having an appropriate attenuation level at every time of measurement, a bandwidth where the sensitivity of the photodetector is high can be constantly used, measurement accuracy at every time of measurement can be improved and consequently the accuracy of the combined particle size distribution can be improved.

DESCRIPTION OF EMBODIMENTS

In the following, a particle size distribution measuring apparatus 100 in one embodiment of the present invention will be described with reference to the drawings.

First, the outline will be described.

Figure 1:
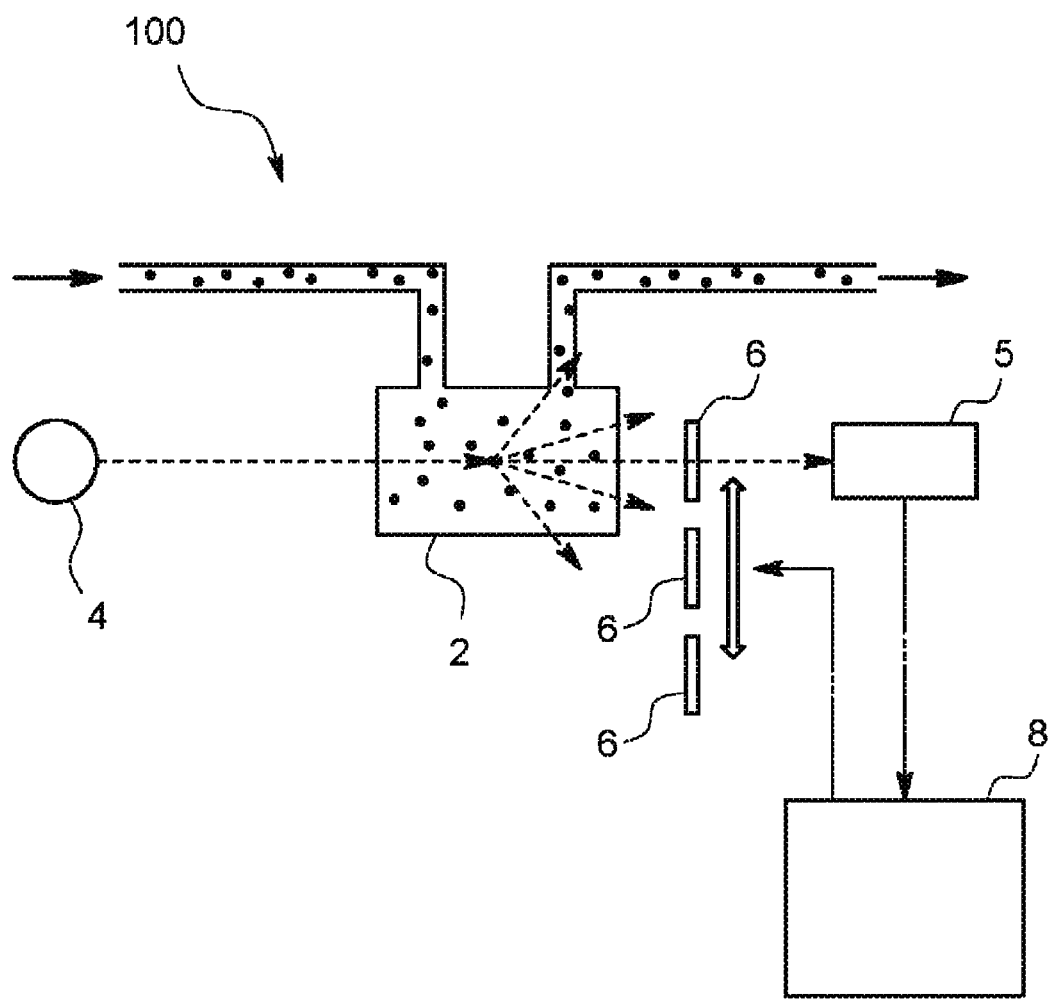
FIG. 1 is a schematic diagram of a particle size distribution measuring apparatus in one embodiment of the present invention.

As illustrated in FIG. 1, the particle size distribution measuring apparatus 100 is one adapted to successively sample a portion of a sample prepared by diffusing a particle group in a liquid dispersion medium such as water, introduce the sampled portion into a cell 2, then at every time of sampling, successively measure the particle size distribution of a portion of the sample in the cell 2 as well as combining particle size distributions obtained at the series of times of measurement, and determines the combined particle size distribution as the particle size distribution of the entire sample. Herein, a dynamic light scattering method is used. That is, the particle size distribution measuring apparatus 100 is adapted to, at every time of measurement, radiate measurement light from a light source 4 to a particle group in a portion of the sample to scatter the measurement light, and detect the intensity of the scattered light by a photodetector 5 to measure the particle size distribution from a fluctuation in the scattered light intensity by an information processing device 8. It is also adapted to arrange a filter member 6 in a light path of the scattered light from the cell 2 to the photodetector 5, making it possible to adjust the intensity of the scattered light received by the photodetector 5 at every time of measurement.

The description will be given more specifically.

Figure 2:
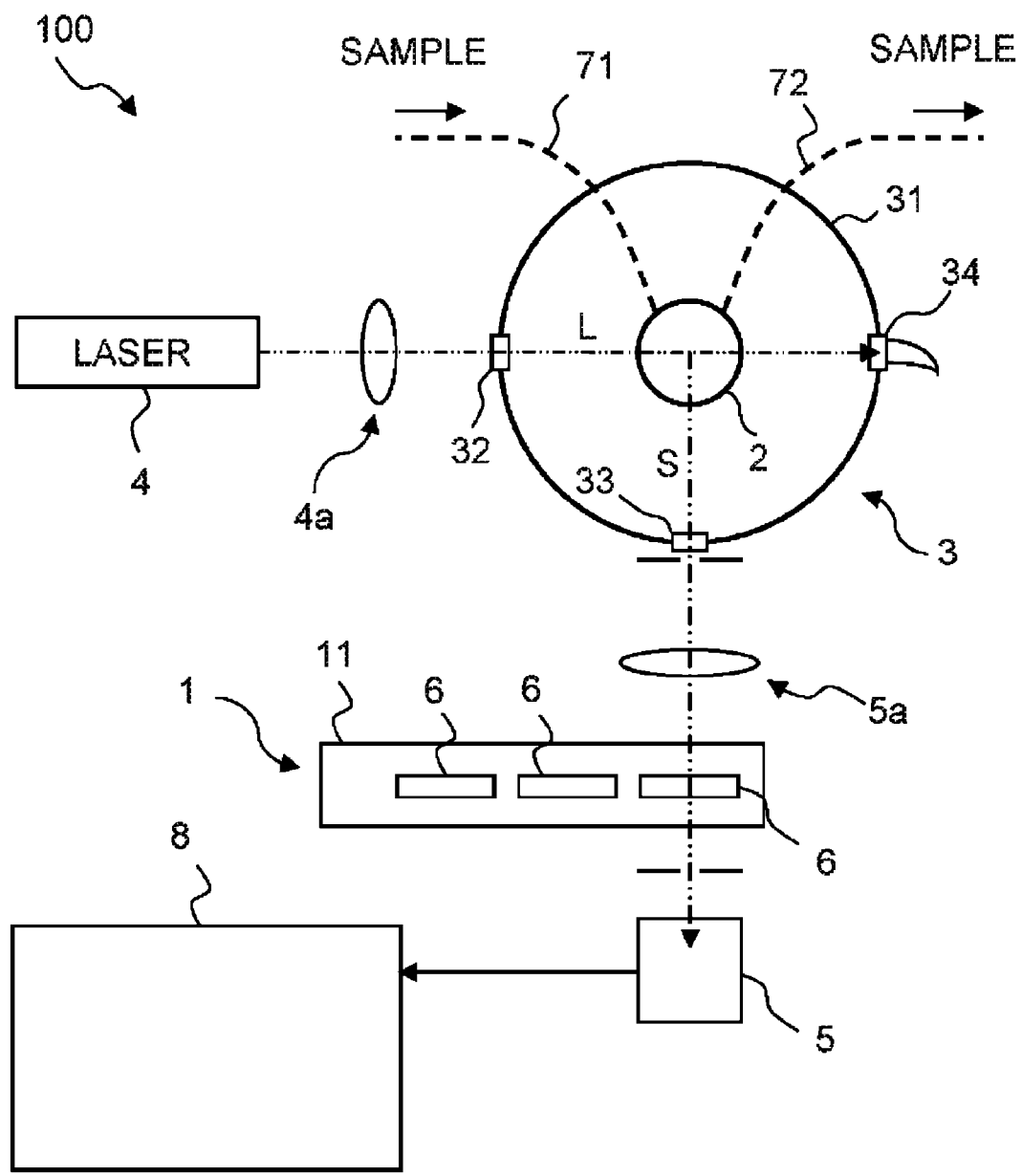
FIG. 2 is an overall diagram more specifically illustrating the particle size distribution measuring apparatus in the same embodiment.

The particle size distribution measuring apparatus 1 is one that, as illustrated in FIG. 2, includes: the cell 2 into which the sample is introduced; the light source 4 adapted to radiate laser light L as the measurement light to the sample in the cell 2 from outside the sample through a bath 3; the photodetector 5 adapted to receive scattered light S emitted from a particle group irradiated with the laser light L, and detect the intensity of the scattered light S attenuated by the filter member 6; the filter member 6 that is arranged in the light path between the cell 2 and the photodetector 5 to attenuate the scattered light S passing therethrough; and the information processing device 8 adapted to receive a signal indicating the scattered light intensity detected by the photodetector 5 and on the basis of a fluctuation in the scattered light intensity and the attenuation level of the filter member 6, measure the particle size distribution of the sample in the cell 2.

The cell 2 is one of a so-called flow cell type that is formed of transparent walls and hollow. The cell 2 is connected with an introduction pipe 71 for introducing the sample into the cell 2 and a lead-out pipe 72 for leading the sample out of the cell 2. In addition, the introduction pipe 71 and the lead-out pipe 72 are respectively provided with unillustrated on-off valves, and it is configured to intermittently introduce and lead the sample into and out of the cell 2 by opening/closing these on-off valves.

The cell 2 is immersed in liquid in the bath 3 (the bath 3 is not necessarily required). The bath 3 is one such that inside a sealable hollow wall body 31, a transparent liquid having an approximate refractive index to or the same refractive index as that of the cell 2 is filled, and in the internal center of the hollow wall body 31, the cell 2 is contained. The wall body 31 is formed of an opaque material, for example, a metallic material, and in the light path of the laser light L and in the light path of the scattered light S, a laser light window 32 and a scattered light window 33 are respectively provided for light transmission. In addition, numeral 34 provided to a part of the wall body 31 on the side opposite to the laser light window 32 denotes a light stopper adapted to attenuate the laser light L having transmitted through the cell 2 to suppress reflection. Also, in this embodiment, the light path of the laser light L and the light path of the scattered light S are made different (in FIG. 1, the respective light paths are adapted to be orthogonal to each other), but may be adapted to be coincident with each other.

The light source 4 is, for example, a semiconductor laser. As the light source, another light source such as an LED, or a halogen lamp is also possible. The laser light L emitted from the light source 4 is condensed onto a predetermined light irradiation area (e.g., the center) inside the cell 2 by a measurement light guiding mechanism 4a. The measurement light guiding mechanism 4a is configured to include, for example, a condenser lens and the like.

The photodetector 5 is, for example, a photo multiplier tube (PMT), but may be another optical sensor such as a CCD or a CMOS. The scattered light S emitted from the particle group is guided to the photodetector 5 by a scattered light guiding mechanism 5a. The scattered light guiding mechanism 5a is one formed by arranging a lens between a pair of pinholes.

The filter member 6 is one that is adapted to attenuate the scattered light passing therethrough at a predetermined attenuation rate and forms a plate shape. Herein, as the filter member 6, an absorptive ND filter formed by dispersing a non-wavelength-selective light absorption material in glass is used. Besides, as the filter member 6, a reflective one is also possible. However, in that case, a structure adapted to prevent reflected light from being radiated to the cell 2 again to generate scattered light is separately required, and therefore the above-described absorptive one is used herein.

Note that in this embodiment, as illustrated in FIG. 2, multiple filter members 6 having different attenuation levels are provided. The multiple filter members 6 are loaded in a filter member changing mechanism 1.

The filter member changing mechanism 1 is one adapted to withdraw the filter member 6 arranged in a predetermined position in the light path of the scattered light and arrange another filter member 6 in the predetermined position. In addition, the filter member changing mechanism 1 is one including: for example, a filter support 11 that supports the multiple filter members 6 having mutually different attenuation levels; and a driving mechanism (not illustrated) configured to include a motor, feed screw mechanism, and the like for moving a desired filter member 6 to the predetermined position.

The information processing device 8 is one configured to, although not illustrated, include: a digital circuit including a CPU, a memory, communication ports (input and output ports), and the like; an analog circuit including an amplifier, a buffer, and the like; and an electric circuit including AD and DA converters serving as a bridge between the digital circuit and the analog circuit. The communication ports are connected with input devices such as a keyboard and a mouse and a display device such as a display although not illustrated, and configured to be operable by an operator.

The information processing device 8 is activated in accordance with a predetermined program stored in the memory, and thereby allows a portion of the sample to be successively introduced into the cell 2 as well as measuring the particle size distribution every time a portion of the sample is introduced into the cell 2. In addition, the information processing apparatus 8 is one that fulfills functions as: a measurement part 81 adapted to combine particle size distributions obtained at the series of times of measurement and thereby calculate the particle size distribution of the whole of portions of the sample introduced at the series of times of measurement; a sampling control part 82 that is adapted to control the introduction and leading out of the sample into and from the cell 2 and includes a drive circuit; a filter control part 83 that is adapted to control the filter member changing mechanism 1 and includes a drive circuit, and the like.

Figure 3:
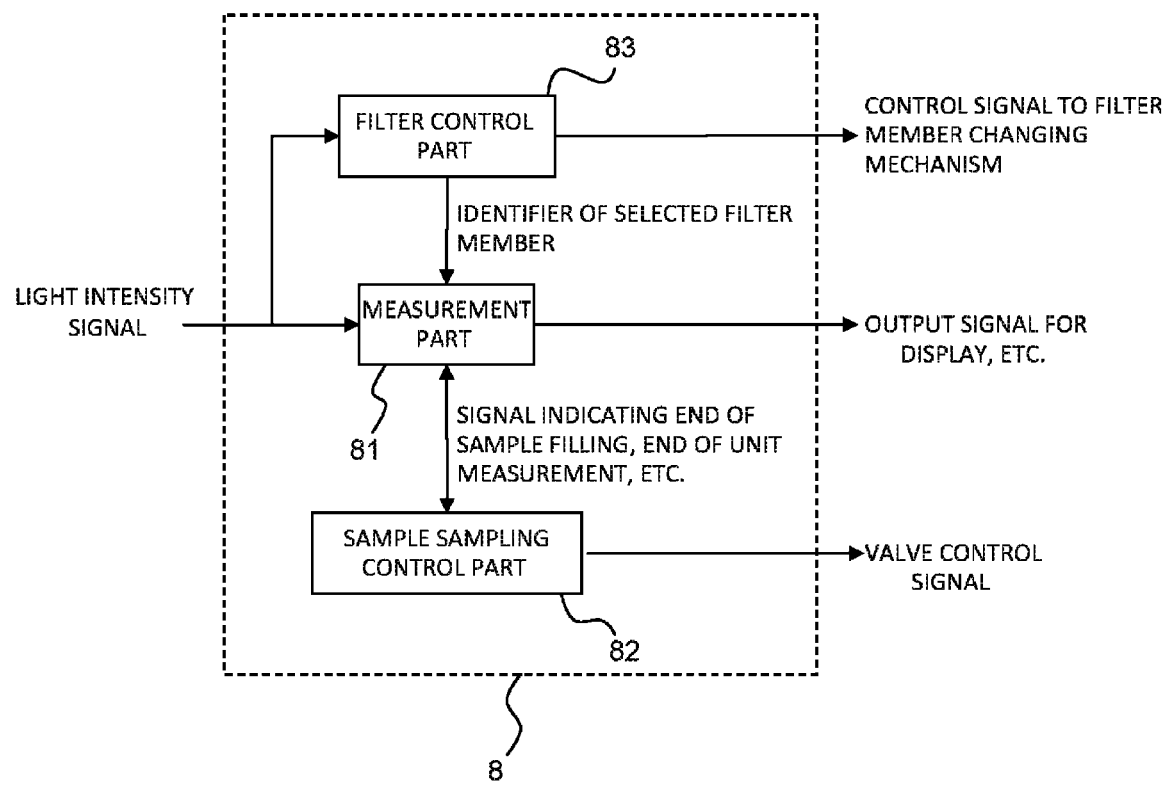
FIG. 3 is a functional block diagram of an information processing device in the same embodiment.

Such functions will be specifically described with reference to FIG. 3 while describing the actions of the information processing apparatus 8. Note that in the following, each of the series of times of measurement is also referred to as unit measurement.

First, an operator sets measurement conditions in accordance with, for example, instructions on a setting screen displayed on the display. The measurement start conditions include, for example, measurement start time, the number of times of unit measurement, a waiting time between adjacent times of unit measurement, and the like.

Then, when the operator clicks, for example, a measurement start icon displayed on the display, the information processing apparatus 8 receives the click to start a series of times of measurement.

In addition, the information processing device 8 sets a filter member 6 having an appropriate attenuation level as the filter member 6 before every time of unit measurement.

That is, the information processing apparatus 8 first drives the valve of the introduction pipe 71 to open the valve for a predetermined constant time, and introduces a portion of the sample into the cell 2 (Step S1). Note that it may be adapted not to set the valve opening time to be constant, but to monitor whether or not a portion of the sample is introduced into the cell 2 to the extent that the particle size distribution is measurable, and depending on a result of the monitoring, drive the valve to open/close it, such as to monitor a transmitted light intensity, and when the transmitted light intensity falls below a predetermined threshold value, stop the valve.

Subsequently, the information processing apparatus 8 receives a light intensity signal outputted from the photodetector 5, and determines whether or not a detected scattered light intensity that is the value of the light intensity signal is within a predetermined range (Steps S2, S4). The predetermined range refers to a range where the sensitivity characteristics of the photodetector 5 are superior, for example, a range where the detected scattered light intensity reproducibly well matches an actual scattered light intensity, and resolution also satisfies the specification characteristics of the photodetector 5.

Then, when the detected scattered light intensity exceeds the upper limit of the predetermined range (hereinafter also referred to as an upper limit threshold value), it can be considered that the intensity of scattered light received by the photodetector 5 exceeds the upper limit of the effective sensitivity the photodetector 5 (or is saturated), and therefore the information processing device 8 replaces the current filter member 6 with another filter member 6 having the next higher attenuation level (Step S3). Note that herein, as the default (initial state) filter member 6, one having a relatively high attenuation level is set. This is to prevent the photodetector 5 from being irradiated with light having a strong intensity without any preparation and thereby damaged.

That is, the information processing device 8 transmits a predetermined control signal, and controls the filter member changing mechanism 1 to withdraw the current filter member 6 from the predetermined position and instead, position another filter member 6 having the next highest attenuation level after the withdrawn filter member 6 in the predetermined position.

After that, the information processing device 8 again receives a light intensity signal from the photodetector 5, and repeats a process of replacing with a filter member 6 having a higher attenuation level until the detected scattered light intensity indicated by the light intensity signal becomes equal to or less than the upper limit threshold value (Steps S2, S3).

On the other hand, when the detected scattered light intensity falls below the lower limit of the predetermined range (lower limit threshold value), in a manner opposite to that employed when the detected scattered light intensity exceeds the value of the upper limit threshold value, the information processing device 8 drives and controls the filter member changing mechanism 1, and repeatedly replaces the filter member 6 with another filter member having a lower attenuation level until the value of the detected scattered light intensity becomes equal to or larger than the lower limit threshold value (Steps S4, S5). In this case, depending on the detected scattered light intensity, the information processing device 8 may drive the filter member changing mechanism 1 until a state where no filter member 6 is positioned (a state where all the filter members 6 are withdrawn from the predetermined position) is reached. Note that when desiring to minimize the risk that the photodetector 5 is irradiated with light having a strong intensity without any preparation and thereby may be damaged, it may be adapted to, as the default (initial state) filter member 6, set one having the highest attenuation level, and repeat only Steps S4 and S5.

When the detected scattered light intensity falls within the predetermined range and predetermined measurement timing comes (Step S6), the information processing device 8 starts unit measurement (Step S7).

Specifically, a detected scattered light intensity is obtained for a predetermined period, and by dividing the value of the detected scattered light intensity by the attenuation level of the filter member 6, a true scattered light intensity is calculated. After that, on the basis of a time fluctuation in the scattered light intensity for the predetermined period, the particle size distribution is measured (calculated).

As a method for calculating the particle size distribution used above, it is only necessary to appropriately use any of a variety of known algorithms, and the detailed description of the method will be omitted here.

Note that it may be adapted to first measure (calculate) a temporary particle size distribution on the basis of the time fluctuation in the detected scattered light intensity, and then by dividing the temporary particle size distribution by the attenuation level of the filter member 6, calculate the true particle size distribution. Also, it may be adapted to, at every time of unit measurement, calculate only a temporary particle size distribution, and when performing the below-described combining computation after the end of respective times of unit measurement, calculate the true particle size distribution. This is because both are equivalent in terms of computation.

In addition, as the attenuation levels of the filter members 6, values publicly announced by a manufacturer of the filter members 6 may be used; however, due to some variations, herein, the attenuation levels of the respective filter members 6 to be loaded are actually obtained by measurement in advance, and pieces of attenuation level data indicating the attenuation levels are listed as a table paired with the identifiers of the filter members 8, respectively and correspondingly, and stored in a predetermined area of the memory. Further, the information processing device 8 is adapted to acquire attenuation level data corresponding to a filter member 6 used at every time of unit measurement from the table, and use an attenuation level indicated by the attenuation level data to calculate the particle size distribution.

A particle size distribution obtained at every time of unit measurement is represented as a spectrum with, for example, the vertical axis as volume or the number of particles and the horizontal axis as a particle size, and data on the particle size distribution is stored in a predetermined area of the memory in connection with information on the time of the measurement or what number the unit measurement is (Step S8).

In this manner, the first time of unit measurement is ended.

After that, the flow returns to Step S1, where the information processing device 8 drives the valves to discharge the portion of the sample having been measured from the cell 2 and instead introduce a new portion of the sample into the cell 2. Then, before the next time of measurement, a filter member 6 having an appropriate attenuation level is selected in the same manner as described above. After that, when predetermined measurement start timing comes, the information processing device 8 performs unit measurement in the same manner as described above, and stores the resulting particle size distribution data in the predetermined area of the memory in connection with information on the time of the measurement or what number the unit measurement is.

In this manner, the information processing device 8 successively performs unit measurement, and when reaching the number of times of measurement set by the operator in the initial measurement conditions, ends the series of times of unit measurement. After that, the information processing device 8 acquires the pieces of particle size distribution data obtained at the respective times of measurement from the memory, and performs the combination computation of them to calculate the particle size distribution of the whole of the portions of the sample introduced into the cell at the series of times of measurement (Steps S9, S10).

As described above, since such a configuration is adapted to, in addition to a basic effect due to combining the series of multiple particle size distribution measurements, select a filter member 6 having an appropriate attenuation level at every time of unit measurement to constantly use the bandwidth where the sensitivity of the photodetector 2 is high, measurement accuracy at every time of unit measurement can be improved and consequently the accuracy of the combined particle size distribution can be dramatically improved.

Note that the present invention is not limited to the above-described embodiment.

It may be configured to, for example, be able to change the emission intensity of the laser light in a multistep manner. In doing so, the change in the emission intensity of the laser light and the filter member changing mechanism are combined with each other, and thereby a measurement range and measurement accuracy can be further enhanced.

The filter member may be adapted to be changed at every time of measurement by an operator. In this case, preferably, the measurement part is configured to, when the scattered light intensity detected by the photodetector is out of the predetermined range, report that the filter member should be replaced. For example, an embodiment adapted to, on the display, display that the detected scattered light intensity exceeds the upper limit threshold value or falls below the lower limit threshold value is conceivable.

The operator is only required to confirm the information on the display and change the filter member to one having a different attenuation level.

When the particle size distribution of a sample has a predetermined criterion such as when the particle size distribution is used for slurry quality management, the information processing device may include a function as a criterion determination part adapted to determine whether or not a particle size distribution measured by the measurement part meets the criterion, and report the result of the determination (such as to display the result).

Examples of a specific algorithm for determining whether or not the measured particle size distribution meets the criterion can include one in which, for example, the absolute value or square value of the intensity difference at each particle size between the criterial particle size distribution and the measured particle size distribution is calculated, and when the value is within a predetermined range, the criterion is met, or otherwise, the criterion is not met.

Figure 4:
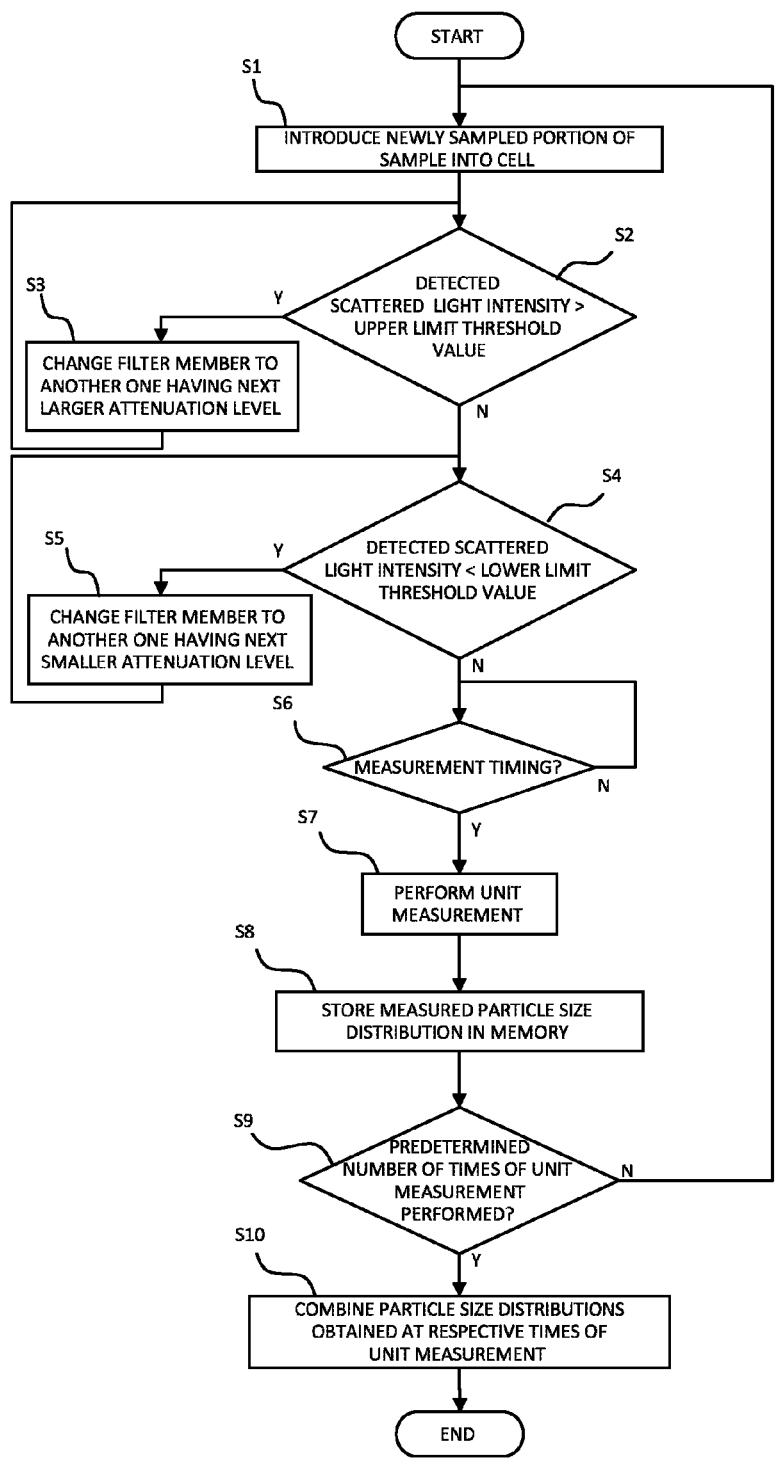
FIG. 4 is a flowchart illustrating the actions of the particle size distribution measuring apparatus in the same embodiment.

Also, when the measurement part 81 performs unit measurement of a sample such as one containing particles and/or impurities (Step S7 in FIG. 4), it may be adapted to further include an autocorrelation function computing part, reference function setting part, autocorrelation function determination part, and use these parts to eliminate an inappropriate scattered light intensity from a scattered light intensity outputted from the photodetector 5.

Specifically, the autocorrelation function computing part performs the Fourier transform of a scattered light intensity outputted from the photodetector 5 to obtain a power spectrum, and computes an autocorrelation function by performing the inverse Fourier transform of the power spectrum. Then, the reference function setting part sets an autocorrelation function serving as a reference (hereinafter referred to as a "reference function") for selecting or not selecting an autocorrelation function computed by the autocorrelation function computing part. Subsequently, the autocorrelation function determination part compares the reference function set by the reference function setting part and an autocorrelation function (hereinafter referred to as "a comparison target function") that is computed by the autocorrelation function computing part and other than the reference function, and determines whether or not the shift amount of the comparison target function from the reference function is within a predetermined range. After that, on the basis of a fluctuation in a scattered light intensity corresponding to a comparison target function of which the shift amount from the reference function is determined to be within the predetermined range, and the attenuation level of a filter member, the particle size distribution of the sample is measured. Note that the reference function is an autocorrelation function obtained by measuring a reference sample different from the sample or an autocorrelation function obtained by performing measurement using the sample. In the latter case, preliminary measurement for obtaining the reference function and regular measurement for obtaining a comparison target function from the sample after the preliminary measurement are performed.

In such a configuration, since the particle size distribution of the sample is measured on the basis of the scattered light intensity corresponding to the comparison target function of which the shift amount from the reference function is determined to be within the predetermined range, a scattered light intensity corresponding to an inappropriate autocorrelation function such as a specific autocorrelation function or an autocorrelation function based on impurities can be eliminated, and therefore the particle size distribution of the sample can be accurately measured.

REFERENCE SIGNS LIST

The filter member may be provided not in the light path of the scattered light but in the light path of the measurement light from the light source to the cell.

Besides, the present invention can be variously modified without departing from the scope thereof.

REFERENCE SIGNS LIST

100: Particle size distribution measuring apparatus
2: Cell
4: Light source
5: Photodetector
6: Filter member
81: Measurement part

The invention claimed is:

1. A particle size distribution measuring apparatus comprising:
    a cell into which a portion of a sample including a medium and particles dispersed in the medium is successively introduced;
    a light source that emits measurement light;
    a photodetector that receives scattered light from particles irradiated with the measurement light and detects an intensity of the scattered light;
    a filter member that is arranged in a predetermined position in a light path of the measurement light from the light source to the cell or a light path of the scattered light from the cell to the photodetector and attenuates the measurement light or the scattered light; and
    a measurement part that on a basis of a fluctuation in the scattered light intensity detected by the photodetector and an attenuation level of the filter member, measures a particle size distribution of a portion of the sample in the cell, wherein:
    the measurement part is one that by measuring a particle size distribution every time a portion of the sample is introduced into the cell as well as combining particle size distributions obtained at respective times of measurement, calculates a particle size distribution of measured portions, the portions being introduced at the multiple times of measurement, respectively; and
    the filter member is configured to be changeable to one having a different attenuation level at every time of measurement.

2. The particle size distribution measuring apparatus according to claim 1, wherein:
    pieces of attenuation level data indicating attenuation levels of respective changeable filter members are stored in a predetermined area of a memory; and
    the measurement part is one that acquires attenuation level data on a filter member used at every time of measurement from the memory, as well as on a basis of an attenuation level indicated by the acquired attenuation level data, measures a particle distribution of a portion of the sample in the cell.

3. The particle size distribution measuring apparatus according to claim 1, the apparatus,
    when the scattered light intensity detected by the photodetector is out of a predetermined range, reporting that the filter member should be replaced.

4. The particle size distribution measuring apparatus according to claim 1, further comprising
    a filter member changing mechanism adapted to withdraw the filter member arranged in the predetermined position and arrange another filter member having a different attenuation level in the predetermined position, wherein
    the filter member changing mechanism is configured to, when the scattered light intensity detected by the photodetector is out of a or the predetermined range, before the measurement, replace the filter member arranged in the predetermined position with one having a different attenuation level.

5. A particle size distribution measuring method using a particle size distribution measuring apparatus comprising: a cell into which a portion of a sample including a medium and particles dispersed in the medium is successively introduced; a light source that emits measurement light; a photodetector that receives scattered light from particles irradiated with the measurement light and detects an intensity of the scattered light; a filter member that is arranged in a predetermined position in a light path of the measurement light from the light source to the cell or a light path of the scattered light from the cell to the photodetector and attenuates the measurement light or the scattered light; and a measurement part that on a basis of a fluctuation in the scattered light intensity detected by the photodetector and an attenuation level of the filter member, measures a particle size distribution of a portion of the sample in the cell, wherein:

the measurement part, by measuring a particle size distribution every time a portion of the sample is introduced into the cell as well as combining particle size distributions obtained at a series of times of measurement, calculates a particle size distribution of measured portions, the portions being introduced at the multiple times of measurement, respectively; and the filter member is changed to one having a different attenuation level at every time of measurement or a part of the multiple times of measurement.

\* \* \* \* \*